(12) United States Patent
Suri

(10) Patent No.: US 8,227,591 B2
(45) Date of Patent: Jul. 24, 2012

(54) NUCLEOTIDE SEQUENCES

(75) Inventor: Anil Kumar Suri, Ali Marg (IN)

(73) Assignee: National Institute of Immunology, Aruna Asaf, Ali Marg, New Delhi (IN)

( * ) Notice: Subject to any disclaimer, the term of this patent is extended or adjusted under 35 U.S.C. 154(b) by 679 days.

(21) Appl. No.: 11/817,252

(22) PCT Filed: Mar. 2, 2006

(86) PCT No.: PCT/IB2006/000445
§ 371 (c)(1),
(2), (4) Date: Aug. 31, 2007

(87) PCT Pub. No.: WO2006/092714
PCT Pub. Date: Sep. 8, 2006

(65) Prior Publication Data
US 2009/0298740 A1 Dec. 3, 2009

(30) Foreign Application Priority Data

Mar. 2, 2005 (IN) .............................. 466/DEL/2005

(51) Int. Cl.
*C07H 21/04* (2006.01)
(52) U.S. Cl. .................. 536/24.5; 536/24.31; 536/24.1; 514/44
(58) Field of Classification Search .................. None
See application file for complete search history.

(56) References Cited

U.S. PATENT DOCUMENTS

2005/0255487 A1* 11/2005 Khvorova et al. ................ 435/6

OTHER PUBLICATIONS

Rana et al. Small interference RNA-mediated knockdown of sperm associated antigen 9 having structural homology with c-Jun N-terminal kinase-interacting protein. Biochem and Biophys Res Comm 2006, vol. 340: 158-164.*

Helm et al. Dedefferentiation precedes invasion in the progression from Barrett's metaplasia to esophageal adenocarcinoma. Clin Cancer Res 2005; 11(7), 2478-2485.*

Jagadish et al. "Characterization of a novel human sperm-associated antigen 9 (SPAG9) having structural homology with c-Jun N-terminal kinase-interacting protein" Biochem. J. (2005) 389, 73-82.

Brummelkamp et al. "Stable suppression of tumorigenicity by virus-mediated RNA interference" Cancer Cell: Sep. 2002—vol. 2, pp. 243-247.

Scanlan et al. "The Cancer/testis genes: Review, standardization, and commentary" Cancer Immunity 4:1 (2004)—Review, found at http://www.cancerimmunity.org/v4p1/031220.htm (1 of 15).

Simpson et al. "Cancer/Testis Antigens, Gametogenesis and Cancer" Nature Reviews|Cancer—vol. 5|Aug. 2005, pp. 615-625.

Yamaguchi et al. "Cell migration in tumors" Science Direct—Current Opinion in Cell Biology 2005, 17:559-564.

Soussi et al. "p53 Website and Analysis of p53 Gene Mutations in Human Cancer: Forging a Link Between Epidemiology and Carcinogenesis" MDI Special Article, Human Mutation 15:105-113 (2000).

Qi et al. "MAP kinase pathways" Cell Science at a Glance, Journal of Cell Science 118, 3569-3572, 2005.

Xia et al. "RNAi suppresses polyglutamine-induced neurodegeneration in a model of spinocerebellar ataxia" Nature Medicine, vol. 10, No. 8, Aug. 2004, pp. 816-820.

Rana et al. "Small interference RNA-mediated knockdown of sperm associated antigen 9 having structural homology with c-Jun N-terminal kinase-interacting protein" Direct Science, Biochemical and Biophysical Research Communications 340 (2006) 158-164.

Sarcevic et al. "Expression of Cancer/Testis Tumor Associated Antigens in Cervical Squamous Cell Carcinoma" Laboratory Investigation, Oncology 2003; 64: 443-449.

Gao et al. "Proliferation and invasion: Plasticity in tumor cells" PNAS | Jul. 26, 2006 | vol. 102, No. 30, pp. 10528-10533.

Shankar et al. "Cloning of a Novel Human Testis mRNA Specifically Expressed in Testicular Haploid Germ Cells, Having Unique Palindromic Sequences and Encoding a Leucine Zipper Dimerization Motif" Biochemical and Biophysical Research Communications, 243 (1998) pp. 561-565 (Article No. RC977943).

Higgins et al. "Gene Expression Patterns in Renal Cell Carcinoma Assessed by Complementary DNA Microarray" American Journal of Pathology, vol. 162, No. 3, Mar. 2003, pp. 925-932.

* cited by examiner

*Primary Examiner* — Kimberly Chong
(74) *Attorney, Agent, or Firm* — Colin P. Cahoon; Celina M. Orr; Carstens & Cahoon, LLP

(57) ABSTRACT

The present invention relates to the field of cancer therapy. More specifically, the invention relates to use of certain nucleotide sequences for the treatment of cancer.

13 Claims, 3 Drawing Sheets

A                              B

| lane1 | Lane2 |

SEQUENCE LISTING

```
<160> NUMBER OF SEQ ID NOS: 18

<210> SEQ ID NO 1
<211> LENGTH: 19
<212> TYPE: DNA
<213> ORGANISM: Artificial
<220> FEATURE:
<223> OTHER INFORMATION: Target Sequences

<400> SEQUENCE: 1
agatctcagt ggatataaa                                                19

<210> SEQ ID NO 2
<211> LENGTH: 19
<212> TYPE: DNA
<213> ORGANISM: Artificial
<220> FEATURE:
<223> OTHER INFORMATION: Target Sequences

<400> SEQUENCE: 2
acagctcata gtagaatta                                                19

<210> SEQ ID NO 3
<211> LENGTH: 19
<212> TYPE: DNA
<213> ORGANISM: Artificial
<220> FEATURE:
<223> OTHER INFORMATION: Target Sequences

<400> SEQUENCE: 3
caaggcggat ctaaagcta                                                19

<210> SEQ ID NO 4
<211> LENGTH: 19
```

```
<212> TYPE: DNA
<213> ORGANISM: Artificial
<220> FEATURE:
<223> OTHER INFORMATION: Target Sequences

<400> SEQUENCE: 4
gttacagatg cgccaaata                                                   19

<210> SEQ ID NO 5
<211> LENGTH: 19
<212> TYPE: DNA
<213> ORGANISM: Artificial
<220> FEATURE:
<223> OTHER INFORMATION: Target Sequences

<400> SEQUENCE: 5
agctcatagt agaattaga                                                   19

<210> SEQ ID NO 6
<211> LENGTH: 19
<212> TYPE: DNA
<213> ORGANISM: Artificial
<220> FEATURE:
<223> OTHER INFORMATION: Target Sequences

<400> SEQUENCE: 6
ggagcagatt tactaggaa                                                   19

<210> SEQ ID NO 7
<211> LENGTH: 19
<212> TYPE: DNA
<213> ORGANISM: Artificial
<220> FEATURE:
<223> OTHER INFORMATION: Target Sequences

<400> SEQUENCE: 7
ttactccgtc cgtcaagaa                                                   19

<210> SEQ ID NO 8
<211> LENGTH: 19
<212> TYPE: DNA
<213> ORGANISM: Artificial
<220> FEATURE:
<223> OTHER INFORMATION: Target Sequences

<400> SEQUENCE: 8
acagctcata gtagaatta                                                   19

<210> SEQ ID NO 9
<211> LENGTH: 19
<212> TYPE: DNA
<213> ORGANISM: Artificial
<220> FEATURE:
<223> OTHER INFORMATION: Target Sequences

<400> SEQUENCE: 9
agaacgccct atatcatta                                                   19

<210> SEQ ID NO 10
<211> LENGTH: 19
<212> TYPE: DNA
<213> ORGANISM: Artificial
<220> FEATURE:
<223> OTHER INFORMATION: Target Sequences

<400> SEQUENCE: 10
agctcatagt agaattaga                                                   19
```

```
<210> SEQ ID NO 11
<211> LENGTH: 19
<212> TYPE: DNA
<213> ORGANISM: Artificial
<220> FEATURE:
<223> OTHER INFORMATION: Target Sequences

<400> SEQUENCE: 11
ttactccgtc cgtcaagaa                                                  19

<210> SEQ ID NO 12
<211> LENGTH: 19
<212> TYPE: DNA
<213> ORGANISM: Artificial
<220> FEATURE:
<223> OTHER INFORMATION: Target Sequences

<400> SEQUENCE: 12
agaagcaact gaagctaca                                                  19

<210> SEQ ID NO 13
<211> LENGTH: 19
<212> TYPE: DNA
<213> ORGANISM: Artificial
<220> FEATURE:
<223> OTHER INFORMATION: Target Sequences

<400> SEQUENCE: 13
gtgtatcagt cgaggtata                                                  19

<210> SEQ ID NO 14
<211> LENGTH: 19
<212> TYPE: DNA
<213> ORGANISM: Artificial
<220> FEATURE:
<223> OTHER INFORMATION: Target Sequences

<400> SEQUENCE: 14
atcagtcgag gtataataa                                                  19

<210> SEQ ID NO 15
<211> LENGTH: 19
<212> TYPE: DNA
<213> ORGANISM: Artificial
<220> FEATURE:
<223> OTHER INFORMATION: Target Sequences

<400> SEQUENCE: 15
tcagtcgagg tataataat                                                  19

<210> SEQ ID NO 16
<211> LENGTH: 19
<212> TYPE: DNA
<213> ORGANISM: Artificial
<220> FEATURE:
<223> OTHER INFORMATION: Target Sequences

<400> SEQUENCE: 16
ataatgggtc atcaactta                                                  19

<210> SEQ ID NO 17
<211> LENGTH: 2515
<212> TYPE: DNA
<213> ORGANISM: Artificial
<220> FEATURE:
<223> OTHER INFORMATION: SPAG9 Sequences
```

-continued

<400> SEQUENCE: 17

```
gacaacttga gctgaaagcg aaaaactatg ctgaccagat tagcagactt gaagaaagag      60
aagcagaact gaagaaggaa tataatgcat tacatcaaag acacactgag atgatccata     120
attatatgga acatttagaa agaacaaaac ttcatcagct ctcagggagt gatcaactag     180
aatccacagc tcatagtaga attagaaaag aacgccctat atcattagga attttcccat     240
tacctgctgg agatggattg cttacacctg atgctcagaa aggaggagag accccctggat    300
ctgagcaatg gaaatttcag gaattaagtc aaccacgttc tcataccagc ctgaaggatg     360
agctttctga tgttagccaa ggcggatcta aagctaccac tccagcatca acagctaatt     420
cagatgtggc aacaattcct actgatactc ccttaaagga agcgaaggam gtgaaggtta     480
cagatgcgcc aaataaatca gagataagca aacacattga agtacaggta gcccaggaaa    540
ctagaaatgt atctactggc tctgctgaaa atgaagaaaa gtcagaagtt caagcaatca    600
tcgaatctac tcctgagctg atatggaca aagatctcag tggatataaa ggttcaagca     660
ctcccaccaa aggcatagag aacaaagctt ttgatcgcaa tacagaatct ctctttgaag    720
aactgtcttc agctggctca ggcctaatag agatgtgga tgaaggagca gatttactag     780
gaatgggtcg ggaagttgag aatcttatat tagaaaatac acaactgttg gaaaccaaaa    840
atgctttgaa catagtgaag aatgatttga tagcaaaagt ggatgaactg acctgtgaga    900
aagatgtgct gcaaggggaa ttggaggctg tgaagcaagc caaactgaaa ctagaggaaa    960
agaacagaga attggaggaa gagcttagga aagctcgggc agaagctgaa gatgcaaggc   1020
aaaaagcaaa agatgacgat gatagtgata ttcccacagc ccagaggaaa cggtttacta   1080
gagtagaaat ggcccgtgtt ctcatggagc gaaaccagta taagagaga ttgatggagc    1140
ttcaggaagc tgttcgatgg acagagatga ttcgggcatc acgagaaaat ccagccatgc   1200
aggaaaaaaa aaggtcaagc atttggcagt ttttcagccg acttttcagc tcctcaagta   1260
acacgactaa gaagcctgaa ccacctgtta atctgaagta caatgcaccc acgtctcatg   1320
ttactccgtc cgtcaagaaa agaagcagca ccttatctca gctccctggg gataagtcca   1380
aagcctttga tttccttagt gaagaaactg aagctagttt agcctcacgc agagaacaaa   1440
agagagagca gtatcgtcag gtaaaagcac atgttcagaa ggaagacggt agagtgcagg   1500
cttttggctg gagtctgcct cagaagtaca aacaggtaac caatggtcaa ggtgaaaata   1560
agatgaaaaa tttacctgtg cctgtctatc tcagacctct ggataaaaaa gatacatcaa   1620
tgaagctgtg gtgtgctgtt ggagtcaama tctggtggga agaccagaga tggtggttct   1680
gttgttggag caagtgtatt ttacaaggat gttgctggtt tggatacaga aggcagtaaa   1740
cagcgaagtg cctctcagag tagtttagat aagttagatc aggaacttaa ggaacagcag   1800
aaggagttaa aaaatcaaga agaattatcc agtctagttt ggatctgtac cagcactcat   1860
tcggctacaa aagttcttat tattgatgct gttcaacctg gcaacatcct agacagtttc   1920
actgtttgca actctcatgt tctgtgcatt gcaagtgtgc caggtgcacg agaaacagac   1980
taccctgcag gagaagatct ttcagaatct ggtcaggtag acaaagcatc tttatgtgga   2040
agtatgacaa gcaacagctc agcagagaca gacagcctgt taggaggcat cacagtggtt   2100
ggttgttctg cagaaggtgt gacgggagct gccacttccc ctagtacaaa tggtgcttct   2160
ccagtgatgg ataaaccacc agaaatggaa gcagaaaata gtgaggttga tgaaaatgtt   2220
ccaacagcag aagaagcaac tgaagctaca gaagggaatg cggggtcagc tgaagacaca   2280
gtggacatct cccaaactgg cgtctacaca gagcatgtbt ttacagatcc tttgggagtt   2340
```

```
cagatcccag aagacctctc cccagtgtat cagtcgaggt ataataatgg gtcatcaact    2400
taggcaactg ggtgaagtgc acaaataaaa ggaaccaaaa taatctcaaa cagtcaaaag    2460
atttccacta attagtgtca ctgtggtgga ttaaaagata dctattcttg tgata         2515
```

<210> SEQ ID NO 18
<211> LENGTH: 765
<212> TYPE: PRT
<213> ORGANISM: Artificial
<220> FEATURE:
<223> OTHER INFORMATION: SPAG9 protein

<400> SEQUENCE: 18

```
Met Ile His Asn Tyr Met Glu His Leu Glu Arg Thr Lys Leu His Gln
1               5                   10                  15

Leu Ser Gly Ser Asp Gln Leu Glu Ser Thr Ala His Ser Arg Ile Arg
            20                  25                  30

Lys Glu Arg Pro Ile Ser Leu Gly Ile Phe Pro Leu Pro Ala Gly Asp
        35                  40                  45

Gly Leu Leu Thr Pro Asp Ala Gln Lys Gly Gly Glu Thr Pro Gly Ser
50                  55                  60

Glu Gln Trp Lys Phe Gln Glu Leu Ser Gln Pro Arg Ser His Thr Ser
65                  70                  75                  80

Ile Lys Asp Glu Leu Ser Asp Val Ser Gln Gly Gly Ser Lys Ala Thr
                85                  90                  95

Thr Pro Ala Ser Thr Ala Asn Ser Asp Val Ala Thr Ile Pro Thr Asp
            100                 105                 110

Thr Pro Leu Lys Glu Glu Asn Glu Gly Phe Val Lys Val Thr Asp Ala
        115                 120                 125

Pro Asn Lys Ser Glu Ile Ser Lys His Ile Glu Val Gln Val Ala Gln
    130                 135                 140

Glu Thr Met Val Ser Thr Gly Ser Ala Glu Asn Glu Glu Lys Ser Glu
145                 150                 155                 160

Val Gln Ala Ile Ile Glu Ser Thr Pro Glu Leu Asp Met Asp Lys Asp
                165                 170                 175

Leu Ser Gly Tyr Lys Gly Ser Ser Thr Pro Thr Lys Gly Ile Glu Asn
            180                 185                 190

Lys Ala Phe Asp Met Thr Glu Ser Leu Phe Glu Glu Leu Ser Ser Ala
        195                 200                 205

Gly Ser Gly Leu Ile Gly Asp Val Asp Glu Gly Ala Asp Leu Leu Gly
    210                 215                 220

Met Gly Arg Glu Val Glu Asn Leu Ile Leu Glu Asn Thr Gln Ile Leu
225                 230                 235                 240

Glu Thr Lys Asn Ala Leu Asn Ile Val Lys Asn Asp Leu Ile Ala Lys
                245                 250                 255

Val Asp Glu Leu Thr Cys Glu Lys Asp Val Leu Gln Gly Glu Leu Glu
            260                 265                 270

Ala Val Lys Gln Ala Lys Ile Lys Leu Glu Lys Asn Arg Glu Leu
        275                 280                 285

Glu Glu Glu Leu Arg Lys Ala Arg Ala Glu Ala Glu Asp Ala Arg Gln
    290                 295                 300

Lys Ala Lys Asp Asp Asp Ser Asp Ile Pro Thr Ala Gln Arg Lys
305                 310                 315                 320

Arg Phe Thr Arg Val Glu Met Ala Arg Val Leu Met Glu Met Gln Tyr
                325                 330                 335
```

```
Lys Glu Arg Leu Met Glu Leu Gln Glu Ala Val Arg Trp Thr Glu Met
                340                 345                 350
Ile Arg Ala Ser Arg Glu Asn Pro Ala Met Gln Glu Lys Lys Arg Ser
            355                 360                 365
Ser Ile Trp Gln Phe Phe Ser Arg Leu Phe Ser Ser Ser Ser Asn Thr
    370                 375                 380
Thr Lys Lys Pro Glu Pro Pro Val Asn Leu Lys Tyr Asn Ala Pro Thr
385                 390                 395                 400
Ser His Val Thr Pro Ser Val Lys Lys Arg Ser Ser Thr Leu Ser Gln
                405                 410                 415
Leu Pro Gly Asp Lys Ser Lys Ala Phe Asp Phe Leu Ser Glu Glu Thr
            420                 425                 430
Glu Ala Ser Leu Ala Ser Arg Arg Glu Gln Lys Arg Glu Gln Tyr Arg
        435                 440                 445
Gln Val Lys Ala His Val Gln Lys Glu Asp Gly Arg Val Gln Ala Phe
    450                 455                 460
Gly Trp Ser Ile Pro Gln Lys Tyr Lys Gln Val Thr Asn Gly Gln Gly
465                 470                 475                 480
Glu Asn Lys Met Lys Asn Leu Pro Val Pro Val Tyr Leu Arg Pro Leu
                485                 490                 495
Asp Lys Lys Asp Thr Ser Met Lys Leu Trp Cys Ala Val Gly Val Asn
            500                 505                 510
Leu Ser Gly Gly Lys Thr Arg Asp Gly Gly Ser Val Val Gly Ala Ser
        515                 520                 525
Val Phe Tyr Lys Asp Val Ala Gly Leu Asp Thr Glu Gly Ser Lys Gln
    530                 535                 540
Arg Ser Ala Ser Gln Ser Ser Leu Asp Lys Leu Asp Gln Glu Leu Lys
545                 550                 555                 560
Glu Gln Gln Lys Glu Leu Lys Asn Gln Glu Glu Leu Ser Ser Leu Val
                565                 570                 575
Trp Ile Cys Thr Ser Thr His Ser Ala Thr Lys Val Leu Ile Ile Asp
            580                 585                 590
Ala Val Gln Pro Gly Asn Ile Leu Asp Ser Phe Thr Val Cys Asn Ser
        595                 600                 605
His Val Leu Cys Ile Ala Ser Val Pro Gly Ala Arg Glu Thr Asp Tyr
    610                 615                 620
Pro Ala Gly Glu Asp Leu Ser Glu Ser Gly Gln Val Asp Lys Ala Ser
625                 630                 635                 640
Leu Cys Gly Ser Met Thr Ser Asn Ser Ser Ala Glu Thr Asp Ser Leu
                645                 650                 655
Leu Gly Gly Ile Thr Val Val Gly Cys Ser Ala Glu Gly Val Thr Gly
            660                 665                 670
Ala Ala Thr Ser Pro Ser Thr Asn Gly Ala Ser Pro Val Met Asp Lys
        675                 680                 685
Pro Pro Glu Met Glu Ala Glu Asn Ser Glu Val Asp Glu Asn Val Pro
    690                 695                 700
Val Pro Thr Ala Glu Glu Ala Thr Glu Ala Thr Glu Gly Asn Ala Gly
705                 710                 715                 720
Ser Ala Glu Asp Thr Val Asp Ile Ser Gln Thr Gly Val Tyr Thr Glu
                725                 730                 735
```

```
His Val Phe Thr Asp Pro Leu Gly Val Gln Ile Pro Glu Asp Leu Ser
            740                 745                 750

Pro Val Tyr Gln Ser Arg Tyr Asn Asn Gly Ser Ser Thr
            755                 760             765
```

NUCLEOTIDE SEQUENCES

FIELD OF THE INVENTION

The present invention relates to the field of cancer therapy. More specifically, the invention relates to use of certain nucleotide sequences for the treatment of cancer.

BACKGROUND OF THE INVENTION

RNA interference (RNAi) is now an umbrella term referring to post-transcriptional gene silencing mediated by either degradation or translation arrest of target RNA. This process is initiated by double-stranded RNA with sequence homology driving specificity.

RNA interference (RNAi) is an evolutionarily conserved post-transcriptional gene silencing (PTGS) mechanism mediated by double-stranded RNA (dsRNA). The dsRNA is processed into small duplex RNA molecules of approximately 21-22 nucleotides (nts) termed small interfering RNAs (siRNAs) by a RNase III enzyme called Dicer. Interaction of siRNAs with a multi-protein complex, termed the RNA-induced silencing complex (RISC), results in sequence specific association of the activated RISC complex with the cognate RNA transcript. This interaction leads to sequence-specific cleavage of the target transcript.

Originally discovered in *Caenorhabditis elegans*, the study of RNAi in mammalian cells has blossomed in the last couple of years with the discovery that introduction of siRNA molecules directly into somatic mammalian cells circumvents the non-specific response vertebrate cells have against larger dsRNA molecules. Emerging as a powerful tool for reverse genetic analysis, RNAi is rapidly being applied to study the function of many genes associated with human disease, in particular those associated with oncogenesis and infectious disease. Use of siRNA as a tool is advancing in almost every field of biomedical research, but some of the most dynamic and exciting applications of siRNA are in cancer research.

Almost all human cancers have accumulated multiple genetic lesions including oncogenes. It is often unknown whether an oncogene is continuously required for tumorigenesis. Furthermore, it is very difficult to target an essential oncogene with drugs without affecting the corresponding nonmutated protooncogene or related factors. RNA interference and the application of small interfering RNAs in mammalian cell culture provide new tools to examine the role of oncogenes in tumor development.

The Applicant has recently cloned a testis specific gene SPAG9 localized on human chromosome 17. It contains coiled coil domains and a leucine zipper motif encoding a protein consisting of 766 amino acids; and has been assigned to UniGene cluster Hs. 129872. Functional analysis of SPAG9 revealed that SPAG9 may have role in one or more events leading to fertilization. Southern hybridization studies suggested that human genome contains single copy of SPAG9 gene having 19 exons. The exons sequence length of SPAG9 varies from 39 to 333. The Applicant sequenced SPAG9 (CAA62987) gene the same bears SEQ ID 17 which encodes the polypeptide (766 aa) and the same bears SEQ ID 18.

Further, based on the above and upon further investigations found that the SPAG9 mRNA is expressed exclusively in normal testis tissue whereas SPAG9 is expressed in a majority of tumors (cancer) and transformed cell lines namely: testis, kidney, uterus, nervous tissue, eye, pituitary, colon, skin, lung, placenta, stomach, urinary bladder, leukopheresis, breast, vulva, pharynx, placenta, bone, prostate and liver.

There is increasing evidence for an immune response to cancer in humans, as demonstrated in part by the identification of autoantibodies against a number of intracellular and surface antigens detectable in sera from patients with different cancer types. The generation of antibodies against SPAG9 in tissues other than testis made the applicant investigate this aspect further and now, the Applicant has now developed novel sequences that are capable of targeting SPAG9 in cancerous tissues.

SUMMARY OF THE INVENTION

Accordingly, in one aspect the invention provides novel nucleotide sequences which are capable of downregulating or interfering with the SPAG9 mRNA which is found to be expressed exclusively in normal testis tissue although SPAG9 is expressed in a majority of tumors (cancer) and transformed cell lines namely: testis, kidney, uterus, nervous tissue, eye, pituitary, colon, skin, lung, placenta, stomach, urinary bladder, leukopheresis, breast, prostate, vulva, pharynx, placenta, bone and liver.

Thus, the invention provides small interfering ribonucleic acid (siRNA) for inhibiting the expression of protein encoded by SEQ ID 17 or an isoform thereof or a polypeptide comprising the said SEQ ID No. 18 in a cell, wherein the siRNA comprises at least 2 sequences that are complementary to each other and wherein a sense strand comprises a first sequence and an anti-sense strand comprises a second sequence comprising a region of complementarity, which is substantially complementary to at least a part of an mRNA encoding a polynucleotide sequence selected from SEQ ID 17.

Some of said novel nucleotide sequences are depicted in Table 1 herebelow.

TABLE 1

| S. No. | Target sequence for sirRNA | Region | Start |
|---|---|---|---|
| 1. | AGATCTCAGTGGATATAAA | ORF | 638 |
| 2. | ACAGCTCATAGTAGAATTA | ORF | 186 |
| 3. | CAAGGCGGATCTAAAGCTA | ORF | 378 |
| 4. | GTTACAGATGCGCCAAATA | ORF | 483 |
| 5. | AGCTCATAGTAGAATTAGA | ORF | 188 |
| 6. | GGAGCAGATTTACTAGGAA | ORF | 771 |
| 7. | TTACTCCGTCCGTCAAGAA | ORF | 1327 |
| 8. | ACAGCTCATAGTAGAATTA | ORF | 186 |
| 9. | AGAACGCCCTATATCATTA | ORF | 209 |
| 10. | AGCTCATAGTAGAATTAGA | ORF | 188 |
| 11. | TTACTCCGTCCGTCAAGAA | ORF | 1327 |
| 12. | AGAAGCAACTGAAGCTACA | ORF | 2240 |
| 13. | GTGTATCAGTCGAGGTATA | ORF | 2373 |
| 14. | ATCAGTCGAGGTATAATAA | ORF | 2377 |
| 15. | TCAGTCGAGGTATAATAAT | ORF | 2378 |
| 16. | ATAATGGGTCATCAACTTA | ORF | 2392 |

In another aspect, the present invention also provides compositions useful for inhibiting cancerous cell proliferation. Such compositions may preferably comprise a small interfering ribonucleic acid (siRNA) for inhibiting the expression of protein encoded by SEQ ID 17 or an isoform thereof or a polypeptide comprising the said SEQ ID No. 18 in a cell, wherein the siRNA comprises at least 2 sequences that are complementary to each other and wherein a sense strand comprises a first sequence and an anti-sense strand comprises a second sequence comprising a region of complementarity, which is substantially complementary to at least a part of an mRNA encoding a polynucleotide sequence selected from SEQ ID 17, together with an appropriate cellular uptake-enhancing peptide segment or agent. Also included in the invention are compositions comprising expression vectors containing the said nucleotides, including nucleic acids encoding sequence ID 1-16.

In one aspect, the invention provides a novel method of inhibiting cellular proliferation of cancer cells which method comprises the step of delivering to the cell a composition comprising a nucleotide selected from SEQ IDs 1 to 16. The said nucleotide sequences may be preferably complexed with a cellular uptake-enhancing agent, and may be delivered in an amount and under conditions sufficient to enter the cell, thereby inhibiting cancerous cell growth/proliferation.

In yet another aspect, the invention provides a novel method of promoting apoptosis which method comprises the step of delivering a composition comprising small interfering ribonucleic acid (siRNA) for inhibiting the expression of protein encoded by SEQ ID 17 or an isoform thereof or a polypeptide comprising the said SEQ ID No. 18 in a cell, wherein the siRNA comprises at least 2 sequences that are complementary to each other and wherein a sense strand comprises a first sequence and an anti-sense strand comprises a second sequence comprising a region of complementarity, which is substantially complementary to at least a part of an mRNA encoding a polynucleotide sequence selected from SEQ ID 17, together with an appropriate cellular uptake-enhancing peptide segment or agent. The said nucleotide sequences may be preferably complexed with a cellular uptake-enhancing agent, and may be delivered in an amount and under conditions sufficient to enter the cell, and cause apoptosis.

As is known, gene silencing by RNA interference (RNAi) operates at the level of mRNA that is targeted for destruction with exquisite sequence specificity. The scheme is shown in FIG. 1A. In principle, any disease-related mRNA sequence is a putative target for RNAi-based therapeutics. To develop this therapeutic potential, it is necessary to develop ways of inducing RNAi by clinically acceptable delivery procedures.

By preventing translational expression of at least part of the protein encoded by SEQ ID 18 or an isoform thereof or expression of polypeptide comprising the said SEQ ID 18. The sequences are useful, in accordance with the inventive method, to prevent expression of SPAG9 protein or proteins produced by polynucleotide sequences comprising SEQ ID 17 and hence cancer cell growth/proliferation.

Thus the novel sequences of the invention that can be delivered to mammalian cells and consequently down regulate or block expression of protein encoded by SEQ ID 17 or an isoform thereof or a polypeptide comprising the said SEQ ID No. 18.

Thus, in another aspect, the invention provides a method of using siRNAs capable of recognizing any of SEQ ID 1 to 16 for inhibiting cellular growth of proliferation of cancerous tissues by delivery of a therapeutically effective amount of the said siRNAs to a subject in need thereof.

BRIEF DESCRIPTION OF THE DRAWINGS

The invention is now illustrated by the following examples and drawings which are only illustrative and not meant to restrict the scope of the invention in any manner. The following accompanying drawings are appended.

DETAILED DESCRIPTION OF THE PREFERRED EMBODIMENT

Example 1

Determination of Endogenous Expression of SEQ ID No. 17 or an Isoform Thereof or a Polypeptide Comprising the Said SEQ ID No. 18 in Cancer Cell Lines A-549 (human lung cancer cells) were grown in RPMI medium (Invitrogen) supplemented with 10% fetal bovine serum (Gibco BRL), 50 units/ml penicillin, and 50 µg/ml streptomycin. The cells were maintained in a humidified 37° C. incubator with 5% CO2. Cancer cells were examined for the expression of protein encoded by SEQ ID 17 or an isoform thereof or expression of polypeptide comprising SEQ ID 18.

The presence protein expressed by SEQ ID 17 or isoform thereof or polypeptide comprising the said SEQ ID 18 in cancer cells was evaluated by indirect immunofluorescence, gel electrophoresis and Western blotting.

Example 2

Indirect Immunofluorescence Assay

Figure 1A:
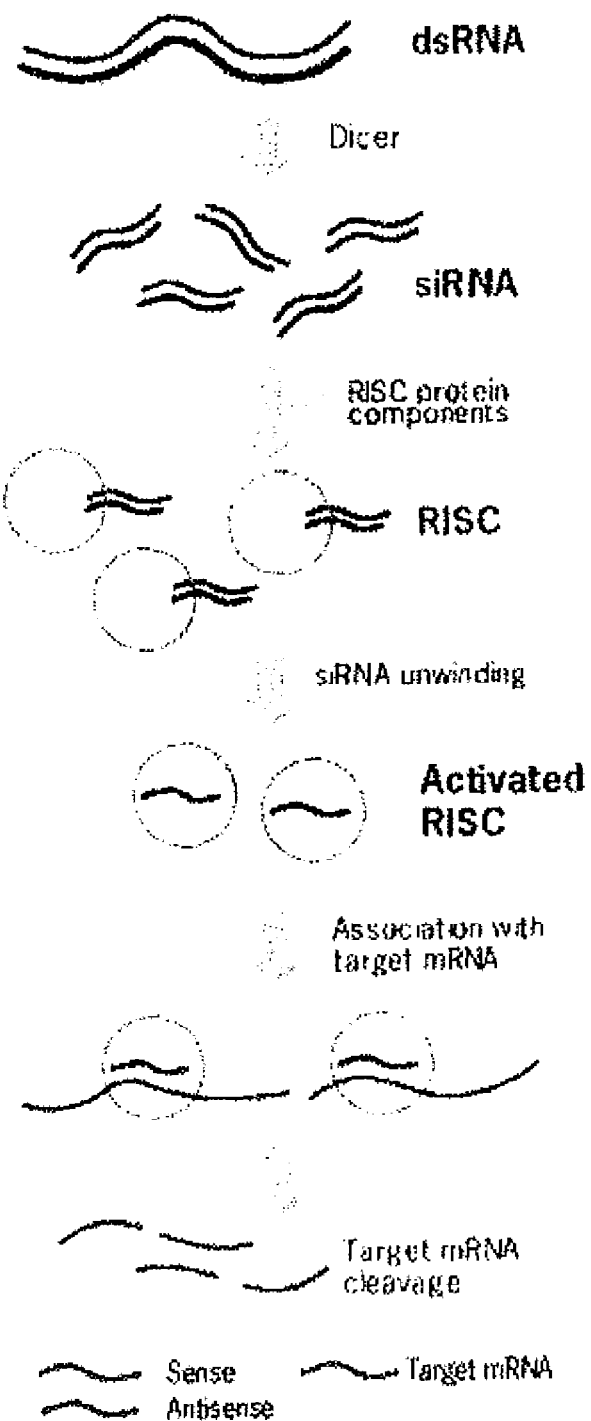
FIG. 1A is a schematic representation of siRNA mediated gene silencing.
Figure 1B:
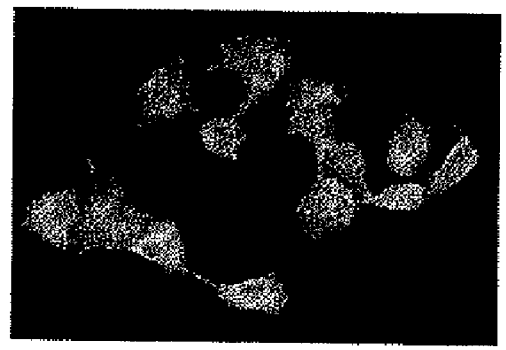
FIG. 1B represents expression of protein comprising SEQ ID No. 17 or an isoform thereof or a polypeptide comprising the said SEQ ID No. 18 in human lung cancer (A549) cell line.

To determine the presence of protein comprising SEQ ID No. 17 or an isoform thereof or a polypeptide comprising the said SEQ ID No. 18 protein in cancer cells, indirect immunofluorescence assay was performed. Cells were probed with antibodies generated against SEQ ID No. 17 or an isoform thereof or a polypeptide comprising the said SEQ ID No. 18 and subsequently with a secondary labelled antibody (fluorescence conjugated antibody). The presence of fluorescence indicated the endogenous expression of protein comprising SEQ ID No. 17 or an isoform thereof or a polypeptide comprising the said SEQ ID No. 18 protein in cancer cell lines (FIG. 1B).

Example 3

Gel Electrophoresis and Western Blotting

The presence of protein comprising SEQ ID No. 17 or an isoform thereof or a polypeptide comprising the said SEQ ID No. 18 protein may detected by Western blotting procedure wherein cancer cell lysate is run on SDS polyacrylamide gel and transferred onto nitrocellulose matrix.

Briefly, the protein solution was diluted with sample buffer. The samples were then loaded onto polyacrylamide gel. After electrophoresis, proteins were transferred onto nitrocellulose membrane. Blocked membrane was probed with antibodies generated against SEQ ID No. 17 or an isoform thereof or a polypeptide comprising the said SEQ ID No. 18 and subsequently with a secondary labelled antibody (enzyme conjugated antibody). Finally, membrane was treated with 0.05% DAB.

Figure 2:
FIG. 2 is a Western Blot analysis of protein expression in human lung cancer (A549) cell lysate.

Western blot analysis of cell lysates from various cancer cell lines demonstrated a strong expression of SEQ ID No. 17 or an isoform thereof or a polypeptide comprising the said SEQ ID No. 18. FIG. 2 which shows a representative photograph of Western Blot analysis of human lung cancer (A549) cell lysate.

Example 4

Inhibition of Protein Expression of SEQ ID No. 17 or an Isoform Thereof or a Polypeptide Comprising the Said SEQ ID No. 18

Preparation of RNAi Plasmids:

A general strategy for constructing an RNAi plasmid involved cloning an inverted repeat of nucleotide-sequences from Seq. ID 1-16 of the SPAG9 into conventional expression vector containing U6 promoter. The siSPAG9 for 638 Seq. ID 1 was designed as under:

```
638 siSPAG9
AGA TCT CAG TGG ATA TAA A (19 mer) TT so
total is 21 mer.
```

Example 5 siRNA Transfection

The siRNA was delivered to various cancerous cell lines and tested for efficacy. The assays were conducted various cancer cell lines of different origin i.e. of ovary, breast, lung, cervix, colon, liver, prostrate, skin, uterus, kidney, urinary bladder, endometrial, bone, pancreas, rectum, pharynx, vulva, placenta, brain, testis, eye, stomach, etc. In all the assays, the siRNA successfully inhibited expression of protein encoded by SEQ ID 17 or an isoform thereof or a polypeptide comprising SEQ ID 18. The siRNAs employed were selected from table 1. A typical example of an assay performed is described below:

Cancer cells were cultured in RPMI (Invitrogen) supplemented with 10% of heat inactivated Fetal calf serum and were grown in 35 mm plates. For siRNA transfection in aqueous medium, the siRNA plasmids were delivered using cellular uptake-enhancing peptide segment or agent. A range of 1 to 12 µg concentration of plasmid DNA was evaluated for inhibiting the expression of SEQ ID No. 17 or an isoform thereof or a polypeptide comprising the said SEQ ID No. 18 and found to be effective in a dose dependent manner.

The reduction in the expression of protein encoded by SEQ ID No. 17 or an isoform thereof or a polypeptide comprising the said SEQ ID No. 18 using siSPAG9 was evaluated by indirect immunofluorescence assay, gel electrophoresis and Western blotting as described above in examples 2 and 3. Further effect on cell viability and apoptosis was also determined in the presence or absence of siSPAG9.

Figure 3:
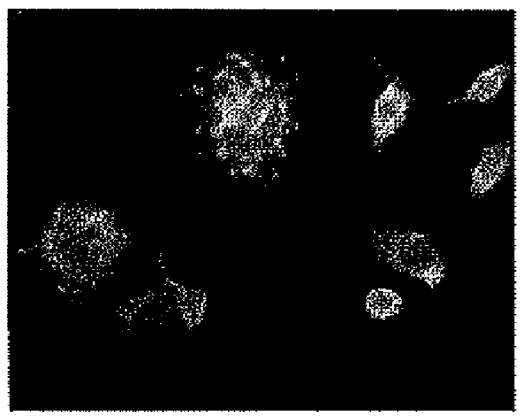
FIG. 3 is an indirect immunofluorescence analysis of human lung cancer (A549) cell line comparing the siSPAG9-treated cancer cells with non-treated cancer cells.
Figure 3:

Indirect immunofluorescence analysis of cancer cells revealed a drastic reduction in the expression of protein encoded by SEQ ID No. 17 or an isoform thereof or a polypeptide comprising the said SEQ ID No. 18 to near background levels in the presence of siSPAG9 as shown in FIG. 3B, whereas strong fluorescence of SEQ ID No. 17 or an isoform thereof or a polypeptide comprising the said SEQ ID No. 18 (FIG. 3A) was observed in non-treated cancer cells.

```
                    Target sequence 638

Apa I                              Spacer 9 mer                            EcoRI
GGG CCC AGA TCT CAG TGG ATA TAA A   TTCAAGAGA   TTT ATA TCC ACT GAG ATC T TTTTTT GAATTC
CCC GGG TCT AGAGTC ACC TAT ATT T    AAGTTCTCT   AAA TAT AGG TGA CTC TAGAAAAAACTTAAG siRNA 638 complete construct with Apa I site at 5' and EcoRI at 3' end.
5' GGG CCC AGA TCT CAG TGG ATA TAA A TTCAAGAGA TTT ATA TCC ACT GAG ATC T TTTTTT GAATTC 3'
3' CCC GGG TCT AGA GTC ACC TAT ATT T AA GTTCTCT AAATAT AGG TGA CTC TAGAAAAAA CTTAAG 5'
```

Therefore the following primers were designed:

```
Forward 638 (Oligo 1)
5' GGG CCC AGA TCT CAG TGG ATA TAA A TTCAAGAGA
TTT ATA Reverse 638 (Oligo 2)
GAATTC A AAA AAA GAT CTC AGT GGA TAT AAA TCT CTT
GAA TTT ATA
```

One step PCR was performed and insert was sub-cloned into conventional expression vector containing U6 promoter.

Figure 4:
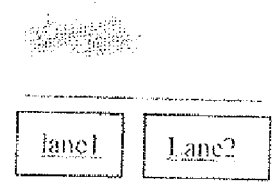
FIG. 4 indicates the Western blot analysis of the human lung cancer (A549) cell lines in the presence or absence of siSPAG9.

In Western blot analysis, a drastic knockdown of SEQ ID No. 17 or an isoform thereof or a polypeptide comprising the said SEQ ID No. 18 expression was observed in SISPAG9 treated cells, whereas the untreated cells revealed no inhibition in the expression of protein encoded by SEQ ID No. 17 or an isoform thereof or a polypeptide comprising the said SEQ ID No. 18. As shown in FIG. 4, lane 1 represents non-treated cancer cells and lane 2 is siSPAG9-treated cancer cells. In lane 1, the cells exhibit expression of protein encoded by SEQ ID No. 17 or an isoform thereof or a polypeptide comprising the said SEQ ID No. 18 whereas the lane 2 cells do not show expression of protein encoded by SEQ ID No. 17 or an isoform thereof or a polypeptide comprising the said SEQ ID No. 18.

Figure 5:
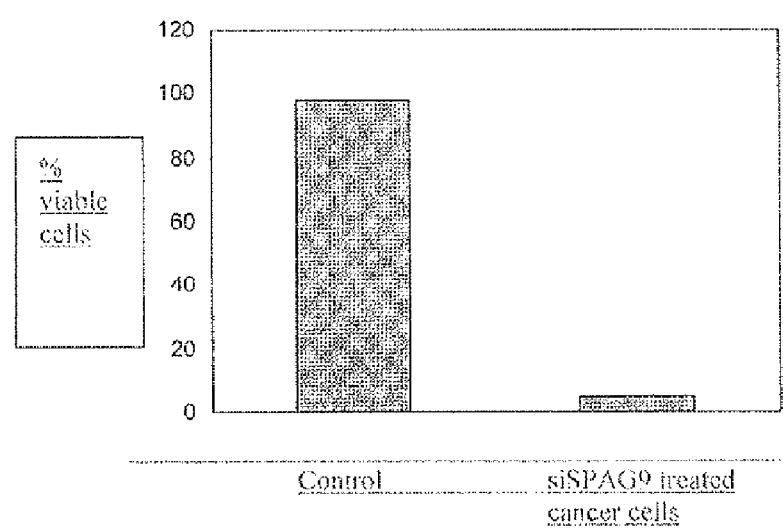
FIG. 5 is a bar chart comparing the percentage of live or viable cells among siSPAG9-treated and non-treated cells.

Cell viability was determined using the vital dye fluorescein diacetate (FDA). Fluorescein diacetate (FDA) and propidium iodide (PI) were added to a cell sample, which was placed in a hemacytometer observed through a fluorescent filter. The cells that appeared bright green (FDA) were counted and recorded as live cells (FIG. 5). The cells were then observed through a rhodamine filter, and cells that appeared bright red (PI) were counted and designated as the number of dead cells. To determine the total cell number, cells were observed under standard light. The percentage of live cells is shown in the bar chart of FIG. 5. The non-treated cells were live, whereas viability of siSPAG9 treated cells is reduced to about 5%.

Apoptosis indicator assay may be used to recognize cells dying as a result of apoptosis rather than accidental forms of cell deaths. siSPAG9 treated and non-treated cancer cells were exposed to two fluorescent dyes: fluorescein diacetate (FDA), which stains cells with intact membranes, and propidium iodide (PI), which characterizes cells with compromised membranes.

The presence of apoptotic cells was confirmed by staining with propidium iodide. The induction of apoptosis was not due to any toxic effects intrinsic to the siSPAG9 formulation.

Figure 6:
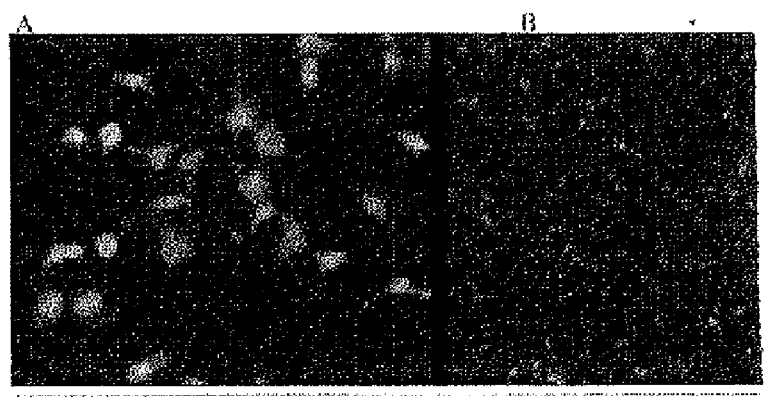
FIG. 6 represents the indirect immunofluorescence analysis of human lung cancer (A549) cells in the presence or absence of siSPAG9 formulation.

This was evident by the absence of apoptotic cells in cultures, wherein no siSPAG9 was introduced. FIG. 6A represents live cells stained with FDA and FIG. 6B represents dead cells after siSPAG9 formulation treatment.

Example 6

Agarose Overlay and Formulation siRNA may be delivered by gel based formulations. Established cultures of cells of tumor origin may be overlaid with an agarose/liposome/siRNA gel formulation without any adverse effects on cell viability or proliferation.

Briefly, Low melting point agarose was used for agarose overlay method of siRNA delivery into cells. To prepare cells for agarose overlay, they were subcultured into either 96-well or 24-well plates and allowed to establish normally in culture for 24 hours. The medium was then removed, and the cells were washed once with optimal medium and overlaid with molten agarose. The agarose was allowed to set at ambient temperature before incubation at 37° C. Finally, normal antibiotic-free cell culture medium was added to each well, and the cells were cultured up to 72 hours. For preparation of agarose/liposome/siRNA formulation, agarose was diluted with preprepared siRNA-liposomes prepared for routine transfection. After careful mixing, the formulation was applied to the cells as for agarose alone. A formulation of agarose/liposomes (without siRNA) was also tested and found to be equivalent to agarose gel alone in terms of lack of effect on cell growth and viability.

Thus, the applicant demonstrates successful topical gel-based delivery of inducers of RNAi to human epithelial cancer cells. Topical induction of RNAi opens an important new therapeutic approach for treatment of human diseases, including cervical cancer and other accessible disorders.

I claim:

1. A small interfering ribonucleic acid (siRNA) for inhibiting the expression of a protein encoded by SEQ ID 17 or an isoform thereof in a cell and polypeptide comprising SEQ ID 18, wherein the siRNA comprises at least 2 sequences that are complementary to each other and wherein a sense strand comprises a first sequence and an anti-sense strand comprises a second sequence comprising a region of complementarity, which is substantially complementary to at least a part of an mRNA encoding a nucleotide sequence from SEQ ID 17, wherein the said siRNA upon contact with a cell expressing protein encoded by SEQ ID 17 or an isoform thereof or expression of polypeptide comprising SEQ ID 18 in a cell and further wherein said first sequence is SEQ ID 13.

2. A cell comprising the siRNA of claim 1.

3. A vector comprising the siRNA of claim 1.

4. A pharmaceutical composition inhibiting expression of protein encoded by SEQ ID 17 or an isoform thereof in a cell, comprising the siRNA of claim 1 together with a cellular uptake enhancing peptide segment or agent.

5. A method of inhibiting cancerous cellular growth/proliferation of cells expressing a protein encoded by SEQ ID 17, an isoform thereof or a polypeptide comprising SEQ ID 18, said method comprising the step of delivering to the cells the composition of claim 4.

6. A method of causing cell death in cells expressing a protein encoded by SEQ ID 17, an isoform thereof or a polypeptide comprising SEQ ID 18, said method comprising the step of delivering to the cell a composition comprising small interfering ribonucleic acid (siRNA) for inhibiting the expression of said protein encoded by SEQ ID 17, said isoform thereof or said polypeptide comprising SEQ ID 18 in a cell, wherein the siRNA comprises at least 2 sequences that are complementary to each other and wherein a sense strand comprises a first sequence and an anti-sense strand comprises a second sequence comprising a region of complementarity, which is substantially complementary to at least a part of an mRNA encoding a polynucleotide sequence from SEQ ID 17, together with an appropriate cellular uptake-enhancing peptide segment or agent and further wherein said first sequence is SEQ ID 13.

7. The method of claim 6 for treatment of cancer, comprising delivery of a therapeutically effective amount of said siRNA to a subject in need thereof.

8. The method of claim 7, wherein said cancerous tissue is mammalian lung cancer tissue.

9. The method of claim 7 wherein said cancerous tissue is selected from the group consisting of ovary, breast, lung, cervix, colon, liver, prostrate, skin, uterus, kidney, urinary bladder, endometrial, bone, pancreas, rectum, pharynx, vulva, placenta, brain, testis, eye, and stomach.

10. A method of inhibiting expression of a protein encoded by SEQ ID 17, an isoform thereof or a polypeptide comprising SEQ ID 18 in a cancer cell, said method comprising the step of delivering to the cell the composition of claim 4.

11. The method of claim 10 wherein said cancer cell is selected from the group consisting of ovary, breast, lung, cervix, colon, liver, prostrate, skin, uterus, kidney, urinary bladder, endometrial, bone, pancreas, rectum, pharynx, vulva, placenta, brain, testis, eye, and stomach.

12. A method of reducing cell viability of cancer cells expressing a protein encoded by SEQ ID 17, an isoform thereof or a polypeptide comprising SEQ ID 18, said method comprising the step of delivering to the cell a composition comprising small interfering ribonucleic acid (siRNA) for inhibiting the expression of said protein encoded by SEQ ID 17, said isoform thereof or said polypeptide comprising SEQ ID 18 in a cell, wherein the siRNA comprises at least 2 sequences that are complementary to each other and wherein a sense strand comprises a first sequence and an anti-sense strand comprises a second sequence comprising a region of complementarity, which is substantially complementary to at least a part of an mRNA encoding a polynucleotide sequence from SEQ ID 17, together with an appropriate cellular uptake-enhancing peptide segment or agent and further wherein said first sequence is SEQ ID 13.

13. The method of claim 12 wherein said cancer cells are selected from the group consisting of ovary, breast, lung, cervix, colon, liver, prostrate, skin, uterus, kidney, urinary bladder, endometrial, bone, pancreas, rectum, pharynx, vulva, placenta, brain, testis, eye, and stomach.

* * * * *